United States Patent [19]  
Merz et al.

[11] 4,100,288  
[45] Jul. 11, 1978

[54] N-TETRAHYDROFURFURYL-NOROXY-MORPHONES, THEIR SALTS, AND ANALGESIC COMPOSITIONS AND METHODS EMPLOYING THEM

[75] Inventors: Herbert Merz, Ingelheim am Rhein; Gerhard Walther, Bingen (Rhein); Adolf Langbein, Ingelheim am Rhein; Klaus Stockhaus, Bingen (Rhein); Helmut Wick, Ingelheim am Rhein, all of Fed. Rep. of Germany

[73] Assignee: Boehringer Ingelheim GmbH, Ingelheim am Rhein, Fed. Rep. of Germany

[21] Appl. No.: 714,045

[22] Filed: Aug. 13, 1976

[30] Foreign Application Priority Data

Aug. 27, 1975 [DE] Fed. Rep. of Germany ....... 2538075

[51] Int. Cl.² .................... A61K 31/485; C07D 489/08
[52] U.S. Cl. ..................................... 424/260; 260/285; 260/347.2; 260/347.8
[58] Field of Search .......................... 260/285; 424/260

[56] References Cited  
U.S. PATENT DOCUMENTS 3,872,127  3/1975  Merz et al. ............................ 260/285

FOREIGN PATENT DOCUMENTS 660,533  9/1965  Belgium.

OTHER PUBLICATIONS

Schidner et al., Chemical Abstracts, vol. 45,2010d (1951).

Primary Examiner—Donald G. Daus  
Assistant Examiner—Diana G. Rivers  
Attorney, Agent, or Firm—Hammond & Littell

[57] ABSTRACT

Diastereoisomers of the compound of the formula

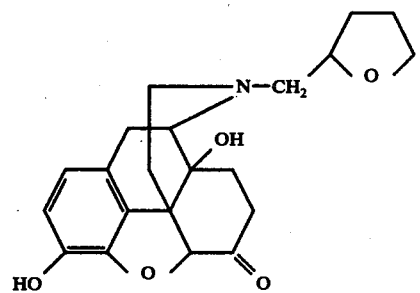

and non-toxic, pharmacologically acceptable acid addition salts thereof; the isomers as well as their salts are useful as analgesics and morphine-antagonists.

3 Claims, No Drawings

N-TETRAHYDROFURFURYL-NOROXYMORPHONES, THEIR SALTS, AND ANALGESIC COMPOSITIONS AND METHODS EMPLOYING THEM

This invention relates to novel diastereoisomeric N-tetrahydrofurfuryl-noroxymorphones and acid addition salts thereof, as well as to various methods of preparing these compounds.

More particularly, the present invention relates to diastereoisomers of the compound of the formula

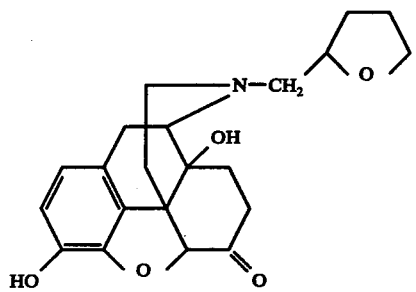

(Ia,Ib)

and non-toxic, pharmacologically acceptable acid addition salts of the said diastereoisomers. The diastereoisomer where the N-substituent is R-tetrahydrofurfuryl is designated as being of the formula Ia, and the diastereoisomer where the N-substituent is S-tetrahydrofurfuryl is designated as being of the formula Ib.

The diastereoisomers of the formulas Ia and Ib are derived from noroxymorphone which is one of the stereoisomers of the base compound of the formula

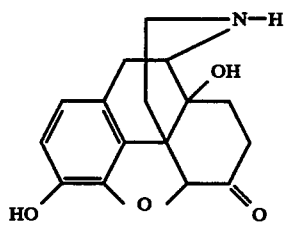

(II)

The stereoisomer is sterically uniformly obtainable from thebaine, and its nomenclature clearly characterizes it.

The N-tetrahydrofurfuryl substituent introduces a new center of asymmetry into the molecule of noroxymorphone; accordingly, the N-tetrahydrofurfuryl-noroxymorphone structure provides for two diastereoisomers (Ia and Ib) which differ from each other only in the configuration at the 2′-carbon atom of the N-tetrahydrofurfuryl substituent. These two diastereoisomers are the subject matter of the present invention, and their steric classification follows from their synthesis from noroxymorphone and an (+)-R- or (−)-S-tetrahydrofurfuryl derivative.

The diastereoisomers of the instant invention may be prepared by the following methods:

Method A

By alkylating levorotatory noroxymorphone of the formula II with a tetrahydrofurfuryl derivative of the formula

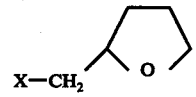

(III)

wherein X is a substituent which can be split off as an anion, such as halogen, preferably chlorine, bromine or iodine, arylsulfonyloxy, alkylsulfonyloxy or (+)-camphor-β-sulfonyloxy of the partial formula

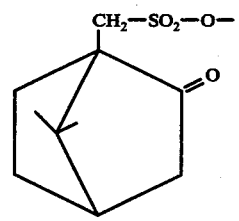

Depending upon whether an R-tetrahydrofurfuryl derivative, an S-tetrahydrofurfuryl derivative or an R,S-tetrahydrofurfuryl derivative of the formula III is used, the reaction product is N-(R-tetrahydrofurfuryl)-noroxymorphone, N-(S-tetrahydrofurfuryl)-noroxymorphone or N-(R,S-tetrahydrofurfuryl)-noroxymorphone, respectively. The latter, that is, the mixture of the two diastereoisomers, may, if desired, be separated by conventional methods, such as by fractional crystallization of the free base or a salt thereof or by column-chromatography.

Specific examples of suitable alkylating agents of the formula III are tetrahydrofurfuryl halides, especially the bromide or iodide, and tetrahydrofurfuryl esters of strong acids, especially of sulfonic acids. With a view toward the directed synthesis of the sterically pure diastereoisomers, it is of great advantage to use as the alkylating agent of the formula III the (+)-camphor-β-sulfonate of R- or S-tetrahydrofurfuryl alcohol, which itself may be obtained by reacting racemic tetrahydrofurfuryl alcohol with (+)-camphor-β-sulfonic acid chloride and separating the mixture of diastereoisomeric esters thus obtained by fractional crystallization.

In order to provide for as complete a reaction as possible of the relatively expensive noroxymorphone with the alkylating agent of the formula III, at least the stoichiometric amount and preferably an excess of the alkylating agent is used. If a relatively slowly reacting alkylating agent is used, such as tetrahydrofurfuryl chloride, it is recommended to add sodium iodide or potassium iodide to the reaction mixture. With a further view toward a smooth and complete reaction, it is useful to effect the alkylation in the presence of an acid-binding agent, such as triethylamine, dicyclohexylethylamine, potassium carbonate, sodium carbonate, calcium oxide, potassium bicarbonate or especially sodium bicarbonate. Although the reaction may be carried out without solvents or in a sufficient excess of the tetrahydrofurfuryl derivative of the formula III, a suitable inert solvent is of advantage. Examples of suitable such solvents are chloroform, toluene, nitromethane, tetrahydrofuran, dimethylformamide or mixtures of these and other solvents. The reaction temperature may be varied within wide limits, the lower limit being given by too slow a reaction speed, and the upper limit by predominance of undesirable side reactions. Tempera-

Method B

By ketal cleavage of a compound of the formula

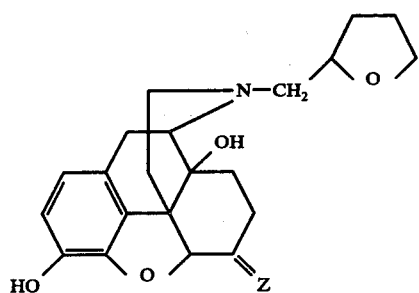

where Z is a ketal group, for example a bisalkoxy group with 1 to 4 carbon atoms in the alkoxy moieties, or an α,ω-dioxyalkylene group of 2 to 4 carbon atoms, particularly ethylenedioxy.

The ketal cleavage is effected by means of dilute acids, advantageously in an organic solvent wherein the ketal of the formula IV as well as the acid are soluble. The temperature limits range from 0° to 100° C.

Method C

By oxidizing or dehydrogenating N-tetrahydrofurfuryl-7,8-dihydro-14-hydroxy-normorphine or N-tetrahydrofurfuryl-7,8-dihydro-14-hydroxy-norisomorphine, respectively of the formula

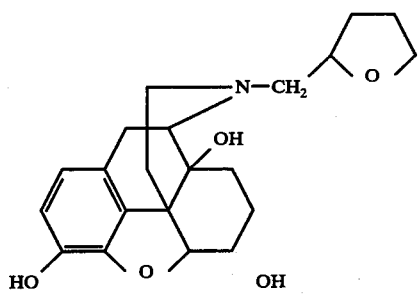

The oxidation or dehydrogenation may be effected by a wide variety of known processes. Examples of suitable oxidation agents are potassium permanganate, chromic acid or silver oxide. More advantageous, however, is the oxidation according to Oppenauer which is preferably carried out with benzophenone and potassium tert-.butylate. The reaction is advantageously performed in a suitable inert solvent the boiling point of which lies within a favorable reaction temperature range, and the reaction mixture is refluxed, the end of the reaction being monitored by thin-layer chromatography. Benzene has proved to be an especially suitable solvent. It is of further advantage to use an excess of benzophenone in order to shift the equilibrium of the reaction in the desired direction.

Method D

By ether cleavage of a compound of the formula

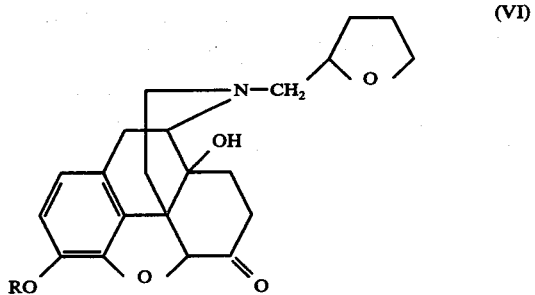

wherein R is lower alkyl of 1 to 4 carbon atoms, especially methyl or ethyl, aralkyl of 7 to 9 carbon atoms, especially benzyl, or alkoxyalkyl of 2 to 6 carbon atoms, especially methoxymethyl, may be subjected to an ether splitting reaction.

Method E

By acid ester and ketal cleavage of a compound of the formula (VII)

wherein $R_1$ and $R_2$, which may be identical to or different from each other, but other than both hydrogen simultaneously, are each hydrogen, aliphatic, aromatic or heterocyclic acyl, particularly acetyl, benzoyl or tetrahydro-2-furoyl, and Y is oxygen or a ketal grouping, for example a bisalkoxy group with 1 to 4 carbon atoms in the alkoxy moieties, or a α,ω-dioxyalkylene group of 2 to 4 carbon atoms, particularly ethylenedioxy.

The ester and ketal cleavage may be carried out in accordance with various known methods. The simplest one is acid hydrolysis, which is preferably effected in aqueous or alcoholic solution. The reaction temperature, which may vary within wide limits, is advantageously between 20° and 100° C.

Method F

By alkaline ester cleavage of a compound of the formula

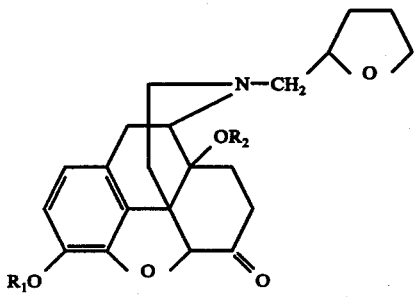 (VIII)

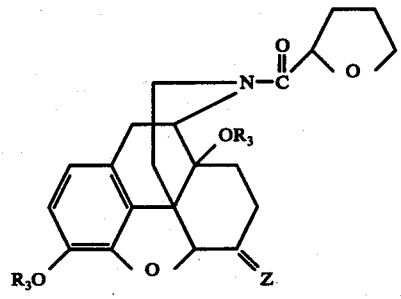 (X)

wherein R₁ and R₂ have the same meanings as in formula VII.

The ester cleavage may be carried out in accordance with various known methods. The simplest one is alkaline hydrolysis, which is preferably effected in aqueous or alcoholic solution. The reaction temperature, which may vary within wide limits, is advantageously between 20° and 100° C.

The reaction products obtained pursuant to methods A to F are isolated by known laboratory methods. If required, the crude products thus obtained may be subjected to known purification processes before they are crystallized in the form of their free bases or acid addition salts.

The optically active tetrahydrofurfuryl bromides of the formula III are prepared from the known optically active alcohols [F. C. Harman and R. Barker, J. Org. Chem. 29, 873–877 (1964)] by bromation with phosphorus tribromide (Org. Synth. 23, 88):

(+)-R-tetrahydrofurfuryl bromide: b.p. 66°–67°/16 mm Hg $[\alpha]_D^{25} = +3.9°$ (c = 5, nitromethane).

(−)-S-tetrahydrofurfuryl bromide: b.p. 67°/16 mm Hg $[\alpha]_D^{25} = +3.8°$ (c = 5, nitromethane).

The diastereoisomeric (+)-camphor-β-tetrahydrofurfuryl sulfonates of the formula III are obtained as reaction products of the reaction of (+)-camphor-β-sulfonic acid chloride with racemic tetrahydrofurfuryl alcohol in pyridine. By crystallization of the resulting mixture of diastereoisomers from carbontetrachloride/petroleum ether (+)-camphor-β-R-tetrahydrofurfuryl sulfonate and (+)-camphor-β-S- tetrahydrofurfuryl sulfonate are separated from each other. The latter, after recrystallization from carbon tetrachloride and petroleum ether, has a melting point of 66° to 67°.

The starting compounds of formula IV are obtained by reacting noroxymorphone or noroxymorphone-ketal of the formula

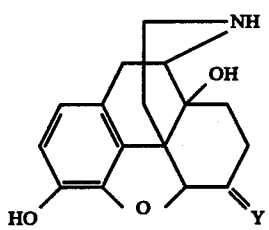 (IX)

wherein Y has the meanings previously defined, with tetrahydro-furan-2-carboxylic acid chloride, optionally followed by ketalization, whereby a compound of the formula wherein Z has the meanings defined above and R₃ is hydrogen or tetrahydro-2-furoyl, is obtained. Then, the compound of the formula X is reduced with lithium aluminum hydride to the starting compound of the formula IV.

A compound of the formula X may also be converted by thionation with phosphorus pentasulfide into a compound of the formula

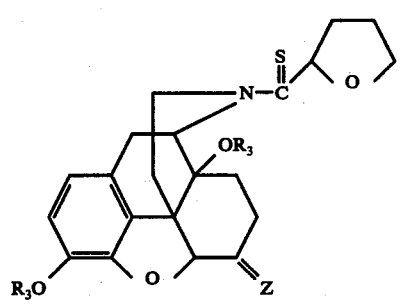 (XI)

wherein R₃ and Z have the previously defined meanings, which in turn may be converted with methyl iodide into a compound of the formula

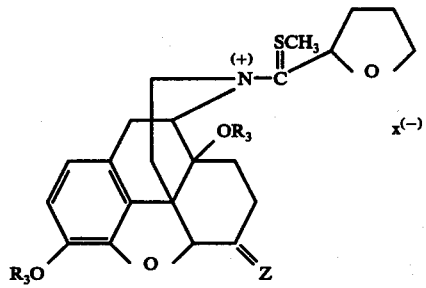 (XII)

wherein R₃ and Z have the above-defined meanings and X⁽⁻⁾ is the anion of an inorganic or organic acid. Compounds of the formulas XI and XII convert by reduction with complex metal hydrides into a compound of the formula IV.

The compounds of the formulas V, VI, VII and VIII are obtained by reacting a corresponding nor-compound with an alkylation agent of the formula III.

If the N-tetrahydrofurfuryl substituent is introduced into the noroxymorphone molecule by method A or other methods, using a racemic tetrahydrofurfuryl compound of the formula III or a precursor thereof, a mixture of the diastereoisomers Ia and Ib is obtained as the reaction product. The individual diastereoisomers may be separated from the mixture by crystallization or column-chromatography.

The diastereoisomers of the formula Ia and Ib are bases and form acid addition salts with inorganic or organic acids. Examples of non-toxic, pharmacologically acceptable acid addition salts are those formed with hydrochloric acid, hydrobromic acid, hydroiodic acid, hydrofluoric acid, sulfuric acid, phosphoric acid, nitric acid, acetic acid, propionic acid, butyric acid, valeric acid, pivalic acid, caproic acid, oxalic acid, malonic acid, succinic acid, maleic acid, fumaric acid, lactic acid, pyruvic acid, tartaric acid, citric acid, malic acid, benzoic acid, p-hydroxy-benzoic acid, salicylic acid, p-amino-benzoic acid, phthalic acid, cinnamic acid, ascorbic acid, 8-chlorotheophylline, methanesulfonic acid, ethanephosphonic acid or the like.

The following examples illustrate the present invention and will enable others skilled in the art to understand it more completely. It should be understood, however, that the invention is not limited solely to the particular examples given below.

EXAMPLE 1

Diastereoisomeric mixture of N-(R-tetrahydrofurfuryl)-noroxymorphone hydrochloride and N-(S-tetrahydrofurfuryl)-noroxymorphone hydrochloride by method A A mixture consisting of 5.75 gm (0.02 mol) of noroxymorphone, 8.25 gm (0.05 mol) of racemic tetrahydrofurfuryl bromide, 6.3 gm (0.075 mol) of sodium bicarbonate and 3.32 gm (0.02 mol) of potassium iodide and 50 ml of dimethylformamide was stirred for 8 hours at 100° C. Subsequently, the reaction mixture was evaporated in vacuo, and the residue was extracted with a mixture of chloroform (100 ml) and water (100 ml). After isolation with the aid of a separating funnel, the aqueous phase was once more extracted with 50 ml of chloroform. The combined chloroform phases were washed twice with 50 ml of water each, dried with sodium sulfate and evaporated in vacuo. The evaporation residue (8 gm of a dark brown oil) consisted of a crude mixture of the two stereoisomers of N-tetrahydrofurfuryl-noroxymorphones. In the thin-layer chromatogram (silicagel, chloroform/methanol/concentrated ammonia = 95:5:0.1) the two diastereoisomers were recognizable, after development with iodine vapor, as spots with the following $R_f$-values: 0.3 (R-tetrahydrofurfuryl derivative) and 0.4 (S-tetrahydrofurfuryl derivative). The evaporation residue was dissolved in about 40 ml of ethanol, and the solution was acidified with 8 ml of ethanolic 2.5 N HCl, whereupon crystallization occurred which was completed by gradual addition of absolute ether (10–20 ml). The mixture was allowed to stand overnight in the refrigerator, was then suction-filtered, and the filter cake was washed first with a mixture of ethanol and ether (1:1) and then with ether. The crystallizate was dried first in the air and then at 80° C. 4.4 gm (53.8% of theory) of a mixture of the diastereoisomeric compounds named in the heading having a melting point of 305° C (decomp.) was obtained. After recrystallization from ethanol the mixture melted at 315° C (decomp.).

EXAMPLE 2

Separation of diastereoisomeric mixture obtained by method A into N-(R-tetrahydrofurfuryl)-noroxymorphone hydrochloride and N-(S-tetrahydrofurfuryl)-noroxymorphone hydrochloride As described in Example 1, 5.75 gm (0.02 mol) of noroxymorphone were reacted with 8.25 gm (0.05 mol) of racemic tetrahydrofurfuryl bromide, and the crude mixture of diastereoisomers obtained after processing of the reaction mixture was separated by column-chromatography. For this purpose it was dissolved in 80 ml of a mobile phase consisting of chloroform/methanol/concentrated ammonia in a volumetric ratio of 90:10:0.1, and this solution was applied to a chromatography column prepared from 1.5 kg of silicagel and the above-indicated mobile phase in the conventional way. The column was eluted with the mobile phase, the eluate was collected in fractions, and the fractions were thin-layer chromatographically analyzed. The fractions comprising pure N-(R-tetrahydrofurfuryl)-noroxymorphone ($R_f$ = 0.3) or pure N-(S-tetrahydrofurfuryl)-noroxymorphone ($R_f$ = 0.4) respectively, were combined and evaporated in vacuo. The free bases obtained as the respective evaporation residues were converted into their hydrochlorides as described in Example 1. 1.4 gm of N-(R-tetrahydrofurfuryl)-noroxymorphone hydrochloride with a melting point of 318° C (decomp.) and 1.2 gm of N-(S-tetrahydrofurfuryl)-noroxymorphone hydrochloride with a melting point of 316° C (decomp.) were obtained. After recrystallization from ethanol, the melting points of the pure diastereoisomers were 321° C (decomp.) and 317° C (decomp.), respectively.

EXAMPLE 3

N-(R-tetrahydrofurfuryl)-noroxymorphone hydrochloride by method A

A mixture consisting of 6.48 gm (0.02 mol) of noroxymorphone hydrochloride, 3.64 gm (0.022 mol) of R-(+)-tetrahydrofurfuryl bromide, 4.2 gm (0.05 mol) of sodium bicarbonate, 3.32 gm (0.02 mol) of potassium iodide and 50 ml of dimethylformamide was heated, while stirring, at 100° C for 20 hours. Thereafter, the reaction mixture was evaporated in vacuo, and the residue was processed by distribution between chloroform and water, as described in Example 1. The evaporation residue of the chloroform phase consisted of the crude reaction product, which was purified by chromatography on aluminum oxide. For this purpose, it was redissolved in 50 to 100 ml of chloroform, and the solution was filtered through a column with 150 gm of aluminum oxide (neutral, activity IV). The column was first eluted with chloroform, then with chloroform/methanol (99:1), and finally with chloroform/methanol (98:2). The eluate was collected in fractions, and the individual fractions were thin-layer chromatographically analyzed. The fractions containing the desired pure substance were combined and evaporated in vacuo. The evaporation residue consisted of N-(R-tetrahydrofurfuryl)-noroxymorphone, which was converted into its hydrochloride in analogy to Example 1. Yield: 2.4 gm (29.7% of theory); m.p. 317° C (decomp.). After recrystallization from a mixture of 100 ml of ethanol and 75 ml of ether the substance melted at 317° C (decomp.). It had a specific rotation of $[\alpha]_D^{25} = -140.5°$ (c = 1.95% of ethanol), which can be lowered to $-124.5°$ by further recrystallizations.

EXAMPLE 4

N-(S-tetrahydrofurfuryl)-noroxymorphone hydrochloride by method A

A mixture consisting of 16.2 gm (0.05 mol) of noroxymorphone hydrochloride, 17.4 gm (0.055 mol) of (+)-camphor-$\beta$-R-tetrahydrofurfuryl sulfonate, 10.5 gm (0.075 mol) of sodium bicarbonate, 7.5 gm (0.05 mol) of sodium iodide and 250 ml of dimethylformamide was heated at 100° C for 20 hours while stirring. Subsequently, the reaction mixture was worked up as described in Example 1, and the free base was converted into its hydrochloride. 6.0 gm (37.1% of theory) of crystallizate were obtained, m.p. 318° C (decomp.); the melting point increased after recrystallization from methanol/ether to 321° C. The substance had a specific rotation of $[\alpha]_D^{25} = -173.1°$ (c = 1.95% of ethanol). which can be raised to $-183.5°$ by further crystallizations.

EXAMPLE 5

Diastereoisomeric mixture of N-(R-tetrahydrofurfuryl)-noroxymorphone hydrochloride and N-(S-tetrahydrofurfuryl)-noroxymorphone hydrochloride by method B a. N-(tetrahydro-2-furoyl)-noroxymorphone (mixture of diastereoisomers)

9.86 gm (0.03 mol) of noroxymorphone hydrochloride were dissolved in 120 ml of methanol, and, while stirring it vigorously, the solution was admixed with a solution of 15 gm of potassium carbonate in 24 ml of water. While continuing to stir the suspension formed thereby, 7.55 gm (0.051 mol) of tetrahydrofuran-2-carboxylic acid chloride were added thereto in 5 portions, the addition of same was distributed over a period of 30 minutes. Subsequently, stirring was continued for 1 hour, and then the reaction solution was evaporated in vacuo. The residue was extracted with a mixture of 150 ml of chloroform and 50 ml of water. After isolation in a separating funnel, the aqueous phase was extracted once more with 50 ml of chloroform, and the combined chloroform phases were washed successively with 50 ml of 1 N HCl and 50 ml of water, dried over sodium sulfate and evaporated in vacuo. The residue consisted of a mixture of the diastereoisomeric N-tetrahydro-2-furoyl)-noroxymorphones.

b. Ketalization of the diastereoisomeric N-(tetrahydro-2-furoyl)-noroxymorphones The evaporation residue of the previous reaction step was kept with 50 ml of ethyleneglycol and 1 gm of p-toluenesulfonic acid at a temperature of 80° C in vacuo (0.01 mm Hg) for 2 hours. Then, the mixture was cooled and stirred into a solution of 15 gm of sodium carbonate in 45 ml of water. The resulting mixture was extracted three times with chloroform (50, 25 and again 25 ml), the combined chloroform extracts were washed with an aqueous sodium carbonate solution, dried with sodium sulfate and evaporated in vacuo. The residue consisted of a mixture of the ethylene ketals of the diastereoisomeric N-(tetrahydro-2-furoyl)-noroxymorphones.

c. Reduction with lithium aluminum hydride

The evaporation residue of the previous reaction step was dissolved in 150 ml of absolute tetrahydrofuran, and the solution as added dropwise to a stirred suspension of 1.52 gm (0.04 mol) of LiAlH$_4$ in 50 ml of absolute tetrahydrofuran on an ice water bath. Then, stirring was continued for 1 hour at room temperature, and afterwards the mixture was refluxed for 2 hours. Subsequently, the reaction solution was cooled and, while stirring, admixed dropwise with 3 ml of water and thereupon extracted with 225 ml of a saturated aqueous diammoniumtartrate solution. After isolation in a separating funnel the tetrahydrofuran phase was evaporated in vacuo. The aqueous phase was extracted three times with chloroform (100, 50 and again 50 ml). The evaporation residue of the tetrahydrofuran phase was dissolved in the combined chloroform extracts, and the resulting solution was washed twice with 50 ml of water each, dried with sodium sulfate and evaporated in vacuo. The residue consisted of a mixture of the ethylene ketals of the diastereoisomeric N-tetrahydrofufuryl-noroxymorphones.

d. Ketal cleavage to form the diastereoisomeric N-tetrahydrofurfuryl-noroxymorphones The end product of the previous reaction step was refluxed with 100 ml of 2 N HCl for 30 minutes. Then, the free base was liberated with ammonia, and the mixture was extracted three times with chloroform (100, 50 and again 50 ml). The combined chloroform phases were washed with water, dried with sodium sulfate and evaporated in vacuo. As described in Example 3, the evaporation residue was purified by column-chromatography on aluminumoxide, and the purified product was converted into a mixture of the diastereoisomeric hydrochlorides. 5.53 gm of crystallizate (55% of theory based on the amount of noroxymorphone hydrochloride) with a melting point of 306° C (decomp.), which increased to 315° C (decomp.) after recrystallization from ethanol/ether, were obtained.

EXAMPLE 6

Diastereoisomeric mixture of N-(R-tetrahydrofurfuryl)-noroxymorphone hydrochloride and N-(S-tetrahydrofurfuryl)-noroxymorphone hydrochloride by method B a. Ethylene ketal of noroxymorphone 13.2 gm (0.04 mol) of noroxymorphone hydrochloride were refluxed with a mixture consisting of 100 ml of absolute benzene, 1 gm of p-toluenesulfonic acid and 40 ml of ethyleneglycol for 2 hours, while stirring vigorously and separating water released by the reaction. Subsequently, the benzene (and part of the glycol) was evaporated in vacuo. The residue was poured into a solution of 5.3 gm (0.05 mol) of sodium carbonate in water. The reaction product separated in crystalline form. After standing overnight in the refrigerator the crystals were suction-filtered off, washed twice with 10 ml of cold water each and dried at 80° C. Yield: 9.0 gm, melting point undefined, but higher than 300° C (decomp.). The mother liquor was extracted three times with 60 ml each of a mixture (1:1) of chloroform and n-butanol, the combined extracts were washed with water, dried over sodium sulfate and evaporated, yielding as the residue an additional 3.0 gm of the ethylene ketal.

b. O,N-di-(tetrahydro-2-furoyl)-noroxymorphone ethylene ketal (mixture of diastereoisomers)

12.0 gm of noroxymorphone ethylene ketal (end product of previous reaction step) were dissolved in 80 ml of methylene chloride, and the solution was admixed with 3.24 ml of triethylamine. While stirring this solution, a solution of 11.85 gm (0.088 mol) of tetrahydrofuran-2-carboxylic acid chloride in 50 ml of methylene chloride was added dropwise thereto over a period of 15 minutes. Subsequently, the mixture was refluxed for 4 hours, then cooled, and thereafter washed in the presence of ice first twice with 40 ml each of 2 N HCl, and then 3 times with 40 ml each of water. After drying of the methylene chloride solution with sodium sulfate it was evaporated in vacuo. The residue consisted of a mixture of the diastereoisomers of O,N-di-(tetrahydro-2-furoyl)-noroxymorphone ethylene ketal (15.2 gm of a yellow oil).

c. Reduction with lithium aluminum hydride 5.0 gm of the evaporation residue of the preceding reaction step (about 0.0095 mol) were dissolved in 40 ml of absolute tetrahydrofuran, and the solution was added dropwise, while stirring and cooling on an ice water bath, to a suspension of 1.3 gm of LiAlH$_4$ (0.034 mol) in tetrahydrofuran. The resulting mixture was then refluxed for 2 hours. Thereafter, the reaction mixture was worked up as described in Example 5(c). The desired product was obtained as the evaporation residue of the chloroform extract.

d. Ketal cleavage

The end product of the preceding reaction step was refluxed with 50 ml of 2 N HCl for 30 minutes. The cooled solution was then admixed with concentrated ammonia, and the precipitated base was extracted three times with 25 ml each of chloroform. The combined chloroform extracts were washed with water, dried with sodium sulfate and evaporated in vacuo. The residue (2.6 gm) was converted into a mixture of the diastereoisomeric N-tetrahydrofurfuryl-noroxymorphone hydrochlorides analogous to Example 1, yielding 1.8 gm (77% of theory based on the amount of ketal of the O,N-diacyl compound) of crystallizate, m.p. 306° C (decomp.), which increased after recrystallization from ethanol/ether to 315° C.

EXAMPLE 7

Diastereoisomeric mixture of N-(R-tetrahydrofurfuryl)-noroxymorphone hydrochloride and N-(S-tetrahydrofurfuryl)-noroxymorphone hydrochloride by method B a. Thionation with phosphorus pentasulfide 10.0 gm (about 0.019 mol) of O,N-di-(tetrahydro-2-furoyl)-noroxymorphone ethylene ketal [Example 6(b)] were dissolved in 100 ml of absolute pyridine, and, after addition of 2.52 gm (0.011 mol) of phosphorus pentasulfide, the reaction mixture was refluxed for 3 hours. Subsequently, the pyridine was distilled off in vacuo, and the residue was extracted with a mixture of 100 ml of methylene chloride and 100 ml of water. After isolation in a separating funnel, the aqueous phase was extracted once more with 50 ml of methylene chloride. The combined methylene chloride phases were washed three times with 30 ml of water each in the presence of ice, dried with sodium sulfate and evaporated in vacuo, leaving a residue 7.5 gm of a yellow oil.

b. Reduction with lithium aluminum hydride 3.75 gm of the end product of the preceding reaction step were dissolved in 50 ml of absolute tetrahydrofuran. The solution was added dropwise to a stirred and ice-cooled suspension of 0.57 gm of LiAlH$_4$ in 20 ml of absolute tetrahydrofuran. The resulting mixture was refluxed for 2 hours and worked up as described in Example 5(c), leaving the desired product as the evaporation residue of the chloroform extract.

c. The end product of the preceding reaction step was subjected to ketal cleavage, as described in Example 5(d). 1.0 gm of the mixture of the diastereoisomers of N-tetrahydrofurfuryl-noroxymorphone hydrochloride, m.p. 314°–315° C, was obtained.

EXAMPLE 8

N-(S-Tetrahydrofurfuryl)-noroxymorphone hydrochloride by method C a. Mixture of N-(S-tetrahydrofurfuryl)-14-hydroxy-dihydronormorphine and N-(S-tetrahydrofurfuryl)-14-hydroxydihydronorisomorphine A mixture consisting of 2.89 gm (0.01 mol) of a mixture of 14 hydroxy-dihydronormorphine and 14-hydroxy-dihydronorisomorphine (obtained by reduction of 14-hydroxy-dihydromorphinone with sodium borohydride), 1.82 gm (0.011 mol) of S-tetrahydrofurfuryl bromide, 1.26 gm (0.015 mol) of sodium bicarbonate and 40 ml of dimethylformamide was heated at 100° C for 24 hours, while stirring. The reaction mixture was worked up as described in Example 1, and purified by chromatography on silicagel (400 gm; chloroform/methanol/concentrated ammonia = 80:20:1). The purified substance was crystallized from acetone and yielded 1.45 gm of a mixture of N-(S-tetrahydrofurfuryl)-14-hydroxy-dihydro-normorphine and N-(S-tetrahydrofurfuryl)-14-hydroxy-dihydro-norisomorphine, which had a melting point of 208°–210° C.

b. N-(S-tetrahydrofurfuryl)-noroxymorphone hydrochloride 1.35 gm (0.0036 mol) of the mixture of N-(S-tetrahydrofurfuryl)-14-hydroxy-dihydronormorphine and N-(S-tetrahydrofurfuryl)-14-hydroxy-dihydronorisomorphine obtained in the preceding step were refluxed together with 8.2 gm of benzophenone and 1.5 gm of potassium tert.butylate in 100 ml of absolute benzene for 2 hours. Subsequently, the reaction mixture was cooled and then extracted 3 times with 10 ml each of 3 N HCl. The combined extracts were made alkaline with ammonia, and the liberated free base was extracted with chloroform (50 ml). The emulsion formed thereby was suction-filtered through diatomaceous earth, the two phases of the filtrate were separated in a separating funnel, and the chloroform phase was dried with sodium sulfate and evaporated in vacuo. The evaporation residue was purified by chromatography on aluminum oxide analogous to Example 3. The purified base was converted into its hydrochloride, which was obtained with a yield of 0.35 gm, m.p. 320° C; after recrystallization from ethanol/ether it melted at 321° C (decomp.).

EXAMPLE 9

Diastereoisomeric mixture of
N-(R-tetrahydrofurfuryl)-noroxymorphone and
N-(S-tetrahydrofurfuryl)-noroxymorphone by method
D a. N-tetrahydrofurfuryl-noroxycodone hydrochloride
(mixture of diastereoisomers)

By reacting noroxycodone hydrochloride (3.38 gm = 0.01 mol) with racemic tetrahydrofurfuryl-bromide a mixture of the diastereoisomers of N-tetrahydrofurfuryl-noroxycodone hydrochloride analogous to Example 1, m.p. 253° C, was obtained.

b. Ether cleavage 0.1 gm of the mixture of diastereoisomers of N-tetrahydrofurfuryl-noroxycodone hydrochloride obtained in the preceding step was heated with 1 gm of pyridine hydrochloride at 200° C for 30 minutes. After cooling, the reaction mixture was dissolved in 2 ml of water, and the solution was gradually admixed with 1 gm of sodium carbonate, and then the pyridine was removed by steam distillation. The residual aqueous solution was extracted three times with equal volumes of chloroform, and the chloroform extracts were combined, washed with water, dried with sodium sulfate and evaporated in vacuo. The residue consisted of a mixture of N-(R-tetrahydrofurfuryl)-noroxymorphone and N-(S-tetrahydrofurfuryl)-noroxymorphone having $R_f$-values 0.3 and 0.4, respectively.

EXAMPLE 10

Diastereoisomeric mixture of
N-(R-tetrahydrofurfuryl)-noroxymorphone and
N-(S-tetrahydrofurfuryl)-noroxymorphone by method
F a.

$O_3,O_{14}$-Diacetyl-N-tetrahydrofurfuryl-noroxymorphone (mixture of diastereoisomers)

The mixture of diastereoisomers was obtained by N-alkylation of $O_3,O_{14}$-diacetyl-noroxymorphone as well as by O-acylation of the mixture of the diastereoisomers of N-tetrahydrofurfuryl-noroxymorphone. It crystallized from isopropanol with a melting point of 160°–161° C.

b. Removal of the acetyl substituents 0.35 gm of the diacetyl compound (mixture of diastereoisomers) was refluxed with 7 ml of methanol and 7 ml of 2 N NaOH for 20 minutes. Subsequently, the reaction mixture was diluted with 20 ml of water and admixed with 20 ml of 2 N ammonium chloride. The mixture was then extracted three times with 20 ml of chloroform each, and the combined chloroform extracts were washed with water, dried with sodium sulfate and evaporated in vacuo, leaving a residue of 250 mgm. The spots of N-(R-tetrahydrofurfuryl)-noroxymorphone and N-(S-tetrahydrofurfuryl)-noroxymorphone at $R_f = 0.3$ and $R_f = 0.4$ were identified in the thin-layer chromatogram.

EXAMPLE 11

N-(S-tetrahydrofurfuryl)-noroxymorphone from
N-(S-tetrahydrofurfuryl)-noroxymorphone
hydrochloride 9.5 gm of N-(S-tetrahydrofurfuryl)-noroxymorphone hydrochloride were shaken with a mixture of 200 ml of chloroform, 100 ml of water and excess ammonia. The separated chloroform phase contained N-(S-tetrahydrofurfuryl)-noroxymorphone which had been liberated from its hydrochloride. After drying with sodium sulfate, the chloroform solution was evaporated in vacuo. The residue was dissolved in a mixture of 15 ml of chloroform and 6 ml of methanol, and the solution was admixed with 20 ml of ether and 20 ml of petroleum ether. N-(S-tetrahydrofurfuryl)-noroxymorphone crystallized out of this solution upon standing in the refrigerator overnight. The crystals were suction-filtered off, and dried at 80° C. Yield: 8.0 gm. The melting point of 125° C did not change after recrystallization.

EXAMPLE 12

Diastereoisomeric mixture of
N-(R-tetrahydrofurfuryl)-noroxymorphone
hydrobromide and
N-(S-tetrahydrofurfuryl)-noroxymorphone
hydrobromide 1.5 gm of the mixture of diastereoisomeric hydrochlorides obtained in accordance with Example 1 were converted into the corresponding mixture of diastereoisomeric bases as described in Example 11, the latter being obtained as the evaporation residue of the chloroform extract. An alcoholic solution of this residue (about 10 ml) was made just acid with ethanolic 65% hydrobromic acid and was then admixed with ether until it began to become turbid. A mixture of the diastereoisomeric hydrobromides (1.0 gm), m.p. 325° C, crystallized out.

The compounds of the present invention, that is, the individual stereoisomers N-(R-tetrahydrofurfuryl)-noroxymorphone and N-(S-tetrahydrofurfuryl)-noroxymorphone, as well as diastereoisomeric mixtures of these, have useful pharmacodynamic properties. More particularly, they exhibit an analgesic and morphine-antagonistic activity component in warm-blooded animals, such as mice.

In the case of N-(R-tetrahydrofurfuryl)-noroxymorphone the analgesic activity component is predominant; this stereoisomer is fifty times more effective as an analgesic than morphine, as determined by the writhing test on mice after subcutaneous administration. As far as the morphine-antagonistic activity component is concerned, the R-tetrahydrofurfuryl isomer exhibits one-fifth to one-third the activity of nalorphine.

On the other hand, while N-(S-tetrahydrofurfuryl)-noroxymorphone exhibits about the same morphine-antagonistic activity as the R-tetrahydrofurfuryl isomer, the analgesic activity component recedes entirely.

As is to be expected on the basis of the morphine-antagonistic activity, the compounds of this invention do not exhibit morphine-like side effects, such as the Straub's tail phenomenon and running-in-circles in mice. Based on prevailing teachings, it can be assumed that such compounds produce no physical dependence. Moreover, even in the highest investigated dosage ranges up to ten thousand times the analgesic $ED_{50}$, the compounds of the present invention produced no undesirable side effects of any kind, which is indicative of an exceptionally large therapeutic ratio of a magnitude not usually associated with other strong analgesics.

For pharmaceutical purposes the compounds of the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.0083 to 1.67 mgm/kg body weight, preferably 0.016 to 0.33 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 13

Tablets

The tablet composition is compounded from the following ingredients:

| | | |
|---|---|---|
| N-(R-Tetrahydrofurfuryl)-noroxymorphone | 20.0 | parts |
| Lactose | 120.0 | parts |
| Corn starch | 50.0 | parts |
| Colloidal silicic acid | 2.0 | parts |
| Soluble starch | 5.0 | parts |
| Magnesium stearate | 3.0 | parts |
| Total | 200.0 | parts |

Preparation:

The noroxymorphone derivative is intimately admixed with the lactose and the corn starch, the mixture is moistened with an aqueous 10% solution of the soluble starch, the moist mass is forced through a 1 mm-mesh screen, the resulting granulate is dried at 40° C, the dry granulate is admixed with the colloidal silicic acid, and the composition is compressed into 200 mgm-tablets in a conventional tablet making machine. Each tablet contains 20 mgm of the noroxymorphone derivative and is an oral dosage unit composition.

EXAMPLE 14

Coated pills

The pill core composition is compounded from the following ingredients:

| | | |
|---|---|---|
| N-(S-Tetrahydrofurfuryl)-noroxymorphone | 15.0 | parts |
| Lactose | 100.0 | parts |
| Corn starch | 95.0 | parts |
| Colloidal silicic acid | 2.0 | parts |
| Soluble starch | 5.0 | parts |
| Magnesium stearate | 3.0 | parts |
| Total | 220.0 | parts |

Preparation:

The ingredients are compounded in the same manner as in Example 13, and the composition is compressed into 220 mgm-pill cores which are subsequently coated with a thin shell consisting essentially of a mixture of sugar, talcum and gum arabic and finally polished with beeswax. Each coated pill contains 15 mgm of the noroxymorphone derivative and is an oral dosage unit composition.

EXAMPLE 15

Suppositories

The suppository composition is compounded from the following ingredients:

| | | |
|---|---|---|
| N-(R-Tetrahydofurfuryl)-noroxymorphone | 10.0 | parts |
| Lactose | 150.0 | parts |
| Suppository base (e.g. cocoa butter) | 1540.0 | parts |
| Total | 1700.0 | parts |

Preparation:

The noroxymorphone derivative is intimately admixed with the lactose, and the mixture is blended with the aid of an immersion homogenizer into the suppository base which had previously been melted and cooled to about 40° C. 1700 mgm-portions of the composition are poured into cooled suppository molds and allowed to harden therein. Each suppository contains 10 mgm of the noroxymorphone derivative and is a rectal dosage unit composition.

EXAMPLE 16

Hypodermic solution

The solution is compounded from the following ingredients:

| | | |
|---|---|---|
| N-(S-Tetrahydrofurfuryl)-noroxymorphone | 1.0 | parts |
| Sodium chloride | 10.0 | parts |
| Double-distilled water   q.s.ad | 1000.0 | parts by vol. |

Preparation:

The noroxymorphone derivative and the sodium chloride are dissolved in the double-distilled water, the solution is filtered until free from suspended particles, and the filtrate is filled under aseptic conditions into 5 cc-ampules which are subsequently sterilized and sealed. Each ampule contains 1.0 mgm of the noroxymorphone derivative, and its contents are an injectable dosage unit composition.

EXAMPLE 17

Drop solution

The solution is compounded from the following ingredients:

| | | |
|---|---|---|
| Mixture of R- and S-diastereoisomers of N-(tetrahydrofurfuryl)-noroxymorphone | 0.70 | parts |
| Methyl p-hydroxy-benzoate | 0.07 | parts |
| Propyl p-hydroxy-benzoate | 0.03 | parts |
| De-mineralized water   q.s.ad | 100.00 | parts by vol. |

Preparation:

The diastereoisomer mixture and the p-hydroxy-benzoates are dissolved in the de-mineralized water, the solution is filtered, and the filtrate is filled into 100 cc-bottles. 10 ml of the solution contain 70 mgm of the diastereoisomer mixture and are an oral dosage unit composition.

Any one of the other compounds of the present invention may be substituted for the particular active ingredient in Examples 13 through 17. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. N-(R-tetrahydrofurfuryl)-noroxymorphone or a non-toxic, pharmacologically acceptable acid addition salt thereof.

2. An analgesic pharmaceutical dosage unit composition consisting essentially of an inert pharmaceutical carrier and an effective analgesic amount of a compound of claim 1.

3. The method of relieving pain in a warm-blooded animal, which comprises perorally, parenterally or rectally administering to said animal an effective analgesic amount of a compound of claim 1.

* * * * *